(12) United States Patent
Bergquist

(10) Patent No.: US 6,242,674 B1
(45) Date of Patent: Jun. 5, 2001

(54) SYNTHETIC CORN HYBRID P129-WX

(75) Inventor: Richard R. Bergquist, El Paso, IL (US)

(73) Assignee: Optimum Quality Grains, L.L.C., Johnston, IA (US)

( * ) Notice: Subject to any disclaimer, the term of this patent is extended or adjusted under 35 U.S.C. 154(b) by 0 days.

(21) Appl. No.: 09/352,551

(22) Filed: Jul. 12, 1999

(51) Int. Cl.⁷ .............................. A01H 5/00; A01H 4/00; A01H 1/00; C12X 1/00
(52) U.S. Cl. .................. 800/320.1; 800/298; 800/275; 800/268; 800/266; 800/264; 800/271; 435/412; 435/424; 435/430; 435/430.1
(58) Field of Search .............................. 800/320.1, 298, 800/275, 271, 266, 268, 264; 435/412, 424, 430, 430.1

(56) References Cited

U.S. PATENT DOCUMENTS

| | | |
|---|---|---|
| 5,675,065 | 10/1997 | Bergquist . |
| 5,704,160 | 1/1998 | Bergquist et al. . |
| 5,706,603 | 1/1998 | Berquist et al. . |
| 5,763,758 | 6/1998 | Bergquist . |
| 5,824,854 | 10/1998 | Bergquist . |
| 5,824,855 | 10/1998 | Bergquist . |
| 5,850,031 | 12/1998 | Bergquist . |
| 5,900,528 | 5/1999 | Bergquist . |
| 5,907,089 | 5/1999 | Bergquist . |
| 5,922,934 | 7/1999 | Bergquist . |
| 5,936,143 | 8/1999 | Bergquist . |

*Primary Examiner*—Gary Benzion
(74) *Attorney, Agent, or Firm*—Bullwinkel Partners, Ltd

(57) ABSTRACT

A synthetic hybrid corn plant having the designation P129-wx, produced by crossing two proprietary Optimum Quality Grain, L.L.C. maize synthetics, P129A-wx-Reid and P129B-wx-Lancaster. P129-wx has the unique property of imparting high oil levels in the grain of certain normal and male sterile hybrids when used as a pollinator. P129-wx is characterized by excellent cold tolerant seedling vigor for rapid emergence in cold soils and excellent early-season adaptability facilitating nicking with early maize hybrids to condition fast dry-down and superior grain quality in the grain arising from the recipient female grain parent. This invention thus relates to the seeds, plants and plant parts of P129-wx, to plants regenerated from tissue culture of the plants or plant parts of P129-wx, to a method of producing P129-wx, and to methods for producing grain or silage using P129-wx as a pollinator.

17 Claims, No Drawings

SYNTHETIC CORN HYBRID P129-WX

FIELD OF THE INVENTION

This invention is in the field of plant breeding. Specifically, this invention relates to a novel synthetic corn hybrid having the designation P129-wx and useful in the proprietary TOPCROSS® grain production system described in U.S. Pat. Nos. 5,704,160 and 5,706,603 by Bergquist et al.

BACKGROUND OF THE INVENTION

Uses Of Corn

Corn (*Zea mays* L.) is an important crop used as a human food source, animal feed, and as a raw material in industry. The food uses of corn, in addition to the human consumption of corn kernels, include products of both the dry milling and wet milling industries. The principal products of dry milling include grits, meal and flour. The principal products of wet milling include starch, syrups, and dextrose. A by product of both dry and wet milling is corn oil, which is recovered from corn germ. As animal feed, corn is used primarily as a feedstock for beef cattle, dairy cattle, swine, poultry, and fish.

Industrial uses of corn mainly consist of the use of corn starch produced by wet milling and corn flour produced by dry milling and the whole kernel fermentation for production of food-grade and industrial use ethanol. The industrial applications of corn starch and flour are based on their functional properties, such as viscosity, film formation ability, adhesiveness, absorbent properties and ability to suspend particles. Corn starch and flour are used in the paper and textile industries, and as components in adhesives, building materials, foundry binders, laundry starches, sanitary diapers, seed treatments, explosives, and oil-well muds. Plant parts other than the corn kernels are also used in industry. For example, stalks and husks can be made into paper and wallboard, and corn cobs can be used for fuel and to make charcoal.

Principles of Conventional Plant Breeding

Virtually all of the commercial corn produced in the United States is produced from hybrid seed. The production of hybrid seed first requires the development of elite corn inbred lines that possess good combining ability to produce agronomically superior hybrids. The majority of hybrid seed produced in the United States is of the single cross type, wherein two inbred lines are intermated, or crossed, to produce what is termed an $F_1$ single cross hybrid. The resulting kernels from this intermating are then sold as seed to commercial growers who plant the seed and harvest the second generation, or $F_2$ grain, for use on farm or for commercial sale.

The production of a conventional single cross hybrid seed involves controlling the direction of pollination from one inbred to the other to assure the production of predominantly hybrid (cross pollinated) seed. Typically directed pollination is accomplished by interplanting separate rows of female corn plants with male corn plants. The female corn plants that are male sterile may be produced by genetic mechanisms which render the corn tassel nonfunctional or by detasseling the plants in the field.

The development of corn hybrids requires the development of homozygous inbred lines or uniform synthetic populations of unique heterotic background, the crossing of these lines or synthetic populations, and evaluation of test crosses. Pedigree breeding and recurrent selection breeding programs are used to develop inbred lines and synthetic populations from breeding populations. Breeding programs combine desirable traits from two or more inbred lines or various broad-based sources into breeding pools from which new inbred lines or synthetic populations are developed by inbreeding or random mating and selection of desired phenotypes. The new inbreds and/or synthetic lines are crossed with other inbred lines and/or synthetic populations and the hybrids from these crosses are evaluated to determine which have commercial value and agronomic usefulness.

Pedigree breeding starts with the crossing of two genotypes, each of which may have one or more desirable characteristics that is lacking in the other or which complements the other. If the two original genotypes do not provide all of the desired characteristics, other sources can be included during the breeding. In the pedigree breeding method, superior plants are selfed or random mated and the resulting seed selected in successive generations. Pedigree records of ancestry are carefully maintained for each family and ear row selection through succeeding generations. In the succeeding generations, the heterozygous condition of the corn germplasm gives way to homozygous true breeding lines as a result of inbreeding and selection. Typically in the pedigree method of breeding, five or more generations of inbreeding and selection is practiced: $F_1$ to $F_2$; $F_2$ to $F_3$; $F_3$ to $F_4$; $F_4$ to $F_5$, etc.

Backcrossing can be used to improve an inbred line by transferring a specific desirable trait from one inbred or source to another inbred that lacks that trait. This can be accomplished, for example, by first crossing a superior inbred (recurrent parent) to a donor inbred (nonrecurrent parent). The donor inbred carries (donates) the appropriate gene(s) for the desired trait to the next generation. After five or more backcross generations with selection for the desired trait, the inbred will be heterozygous for loci controlling the characteristic being transferred, but will be like the superior parent for most or almost all other genes. The last backcross generation can be selfed to produce a pure breeding progeny for the gene(s) being transferred.

An important consequence of the homozygosity and homogeneity of the inbred lines is that the hybrid between any two inbreds will always be the same. Once the inbreds or synthetics that give the best hybrid have been identified, the hybrid seed can be reproduced indefinitely as long as the homogeneity of the inbred or synthetic parents is maintained.

A synthetic hybrid consists of an array of similar genotypes that were identified from intercross tests and bulked into a random mating population having a desired phenotype. The intercrosses between two different heterotic groups results in the continuous production of a specific synthetic hybrid of desired phenotype.

As previously noted, a single cross hybrid is produced when two unrelated inbred or synthetic lines are crossed to produce the $F_1$ progeny. A three-way cross hybrid is produced from three inbred lines (or synthetics) where two of the inbred lines (or synthetics) are crossed (A×B) and then the resulting $F_1$ hybrid is crossed with the third inbred (or synthetics) (A×B)×C. A double cross hybrid is produced from four inbred lines (or synthetics) by crossing pairs (A×B) and (C×D) and then crossing the two $F_1$ hybrids (A×B)×(C×D).

Much of the hybrid vigor exhibited by $F_1$ hybrids is lost in the next generation ($F_2$). Consequently, seed (grain) from hybrid varieties is not used for planting stock.

The objective of typical plant breeding is to combine in a single variety/hybrid the desirable traits of the parental lines. For field crops such as corn, these desirable traits may include resistance to diseases, insects, herbicide tolerance, and tolerance to heat and drought, reducing time to crop maturity, and improved agronomic quality. With mechanical harvesting of many crops, uniformity of plant characteristics such as germination time and stand establishment, growth rate, and fruit/seed size are also desirable.

The problem with conventional breeding techniques is that there are several grain quality traits, such as high oil content, that cannot readily be combined in a high-yielding single cross hybrid. By contrast, synthetic hybrids, such as the one described herein, when used as a pollinator in the TOPCROSS® grain production system, can impart desirable grain quality characteristics, such as high oil content, to the resulting $F_1$ grain without significant loss in yield.

Synthetic Varieties

Corn has male flowers, located on the tassel, and female flowers, located on the ear, of the same plant. Because of this monoecy, corn plants can be bred by both self-pollination and cross-pollination techniques. Corn is self-pollinated if pollen from one flower is transferred to the same or another flower on the same plant. Corn is cross-pollinated if the pollen comes from a flower on a different plant.

Plants that have been self-pollinated and selected for uniform type over many generations become homozygous at almost all gene loci and produce a uniform population of true breeding progeny. Cross pollination between two homozygous lines produces a uniform population of hybrid plants that nevertheless may be heterozygous for many gene loci. A cross between two plants that are each heterozygous for a number of gene loci will produce a population of hybrid plants that differ genetically and will not be uniform.

Natural pollination occurs when wind blows pollen from tassels to silks that protrude from tops of the incipient ears on plants of the same genotype and different genotype, resulting in both self- and cross-pollination. When a population of genotypes are combined from all possible intercrosses among a number of selected genotypes and are allowed to open pollinate, the result is called a synthetic variety. A synthetic variety is made up of genotypes which previously have been tested for their ability to produce a superior progeny when crossed in all combinations.

Corn plants may be maintained as an outcrossing synthetic population that is much less homogeneous than a self-pollinated group. Every plant in such a group is certain to be heterozygous at many or most loci, and this heterozygosity must either be maintained during a breeding program or restored at the end of the program, if productivity is to be satisfactory. The main requirement in maintaining a synthetic line is that a sufficient number of plants of heterozygous background be maintained to recover the gene frequencies that are desired for the synthetic population so as to prevent genetic drift toward undesired gene frequencies.

The Desirability of High Oil Content Grain

The concentration of oil in most varieties of corn ranges from less than 3.0 percent to 4.5 percent at 0% moisture. Embryos of ordinary corn can contain 30 percent oil, while embryos of high oil corn strains can contain as much as 50 percent oil and are much larger in size than ordinary corn embryos.

There are several reasons for wanting to develop a method for growing corn that is high in oil content. First, corn oil is a premium oil and regularly more valuable than starch, the other major component of corn kernels. Second, high oil corn possesses a higher available energy content than ordinary corn, and thus is a more valuable feed for poultry and livestock. In animal feeding trials it has been found that less high oil corn is required per unit of gain than is required with ordinary corn. In addition, high oil corn requires substantially less soybean meal to balance a typical animal diet, and may be used to replace oil containing additives in animal feed.

Additional impetus was given to breeding corn for high oil by the development of wide-line nuclear magnetic resonance spectroscopy (NMR) and near-infrared spectroscopy (NIR) as analytical tools for the nondestructive analysis of bulk or single kernel samples that can be carried out in as little as two seconds. The development of such tools made it much easier and much quicker to determine the oil content of grain, thereby encouraging experimentation in the area of breeding for high oil.

Thus there exists at present a growing market for corn having high oil, increased protein and other special end-use properties which is not met by corn of standard composition. The diverse types of corn available to plant breeders provides a potential for modification of quality and quantity of grain protein, starch, and oil. Corn now can be developed to more precisely meet the specific nutritional requirements of animals or to meet particular industrial needs.

The TOPCROSS® Grain Production System

Unfortunately, high oil is a property that cannot readily be achieved in a high yielding single-cross hybrid. This is because oil content, while being a moderately heritable trait, is influenced by a series of oil genes that have additive effects on oil content and occur at a complex of loci in at least eight linkage groups that influence the amount of oil in the grain progeny. Obtaining a hybrid having all or most of these oil genes can take many years of breeding. Further increasing the difficulty of breeding for high oil content is the fact that the grain yield of higher oil hybrids is generally inferior when compared to elite dent corn hybrids.

A method of producing a high yield of corn having high oil content without requiring years of breeding is described in Bergquist et al. U.S. Pat. No. 5,704,160. The primary aspect of this method, known as the TOPCROSS® grain production system, is the interplanting of a pollinator corn plant possessing the characteristics for significantly increasing oil and protein levels in the resulting grain with a male sterile hybrid corn plant. The resulting grain possesses an oil content much higher than would be expected for self- or cross-pollination of the fertile version of the hybrid corn plant.

In practice, the seed of the pollinator with improved grain quality traits is blended in small amounts with seed of an elite male sterile grain parent hybrid, but with sufficient pollinator seed to permit abundant pollen production for fertilization of the male sterile grain parent hybrid. The relatively low ratio of pollinator seed to male sterile grain parent seed (less than one pollinator plant to every three grain parent plants) takes advantage of the higher grain yield potential of the elite grain parent hybrid while assuring a sufficient population of pollinator plants to pollinate the male sterile grain parent plants.

Need for Superior Pollinators

Critical to the success of the TOPCROSS® grain production system is the use of a pollinator capable of enhancing the grain quality traits of the $F_1$ offspring. To obtain such pollinators, the corn breeder must select and develop corn plants that have the traits that result in superior inbred and synthetic parental lines.

The pollinator for the TOPCROSS® grain production system need not be genetically homozygous (inbred) or even uniform in appearance, and need not be selected for genetic combining ability with female plants. However, the pollinator should have uniform desirable grain quality characteristics, such as high oil, that will influence the grain quality characteristics of the $F_1$ offspring, and the ability to pollinate the female plants. A hybrid obtained by crossing two synthetic populations of different heterotic backgrounds results in a synthetic hybrid with predictable heterozygosity and genetic variability among plants that is particularly useful as a male pollinator in blends with male sterile hybrid grain parents in the TOPCROSS® grain production system. Some genetic variability is desirable because it extends the flowering period of the pollinator. P129-wx was developed to achieve these characteristics.

Advantages of Synthetic Hybrids

The use of synthetic hybrids (such as P129-wx) as TOPCROOSS® grain production system pollinators affords a number of advantages over the use of inbreds, hybrids produced from single crosses, or hybrids produced from three way crosses. For instance, synthetic hybrids can be developed more rapidly than commercial hybrids. Specifically, the use of a synthetic population can more rapidly establish stability of dominant oil genes, thus by-passing the many generations of inbreeding that is required to produce inbreds for making single cross hybrids.

Second, synthetic hybrids often have excellent vigor comparable to that of commercial hybrids. Inbreds, by contrast, typically lose vigor with each successive generation of inbreeding. This is an important advantage of synthetics because pollinator vigor is critical for ample pollen shed at the time of silking in the TOPCROSS® grain production system. Synthetic hybrid P129-wx expresses cold vigor in seedling growth stages greater than even most open pollinated synthetic populations.

Third, a synthetic variety, utilizing heterosis in which pollination control is a factor, is more likely to disperse pollen over a longer period of time than a single cross hybrid. The predictable greater variability of synthetic varieties as compared with single crosses permits more flexibility to meet the changing growing conditions typical of field production. In addition, because of the longer flowering period, fewer synthetic pollinators need be developed to be used in blends with many different grain parents.

Fourth, the synthetic hybrid pollinator is more easily produced during periods of heat and drought stress on dryland production than a single-cross hybrid using less vigorous inbred seed stocks. For example, in non-irrigated dryland field tests conducted during 1993 and 1994, production of synthetic hybrid seed remained relatively constant at about 55 bushels per acre despite the fact that rainfall accumulation during the critical months of May, June and July fell from 40.84 cm in 1993 to 13.82 cm in 1994. Over the same period, single cross seed production using inbred seed stocks fell to less than 25 bushels per acre in 1994 from 55 bushels per acre in 1993.

Fifth, the single cross synthetic hybrid pollinator which results from the cross of two parental synthetic populations, A×B, is more quickly produced in a single generation compared to a three-way cross pollinator (A×B)C that requires an additional plant generation to produce the hybrid three-way cross pollinator. For example, the A×B synthetic hybrid is simply produced in a single plant growing generation in the production of P129-wx single-cross synthetic hybrid while the three-way cross synthetic hybrid pollinator would require an additional plant generation to produce the final hybrid (A×B) crossed to the parental C-population to produce a synthetic three-way hybrid cross designated (A×B)C.

SUMMARY

According to the invention, there is provided a novel synthetic corn hybrid, designated P129-wx, that when used to pollinate an elite male sterile hybrid grain parent, produces commercial grain exhibiting improved quality grain traits, including waxy grain phenotype, high oil and high protein. Furthermore, when P129-wx is used to pollinate male sterile hybrid grain parents that are harvested as whole plants at approximately 50% plant moisture, it produces commercial fodder that expresses improved feed efficiency and rate of weight gain.

P129-wx is characterized by excellent cold tolerant seedling vigor for rapid emergence in cold soils and excellent early-season adaptability facilitating nicking with early maize hybrids to condition fast dry-down and superior grain quality in the grain arising from the recipient female grain parent.

This invention thus relates to the seeds, plants and plant parts of P129-wx, to plants regenerated from tissue culture of the plants or plant parts of P129-wx, to a method of producing P129-wx by crossing P129A-wx-Reid and P129B-wx-Lancaster synthetics, and to methods for producing grain or silage using P129-wx as a pollinator.

DEFINITIONS

In the description and examples that follow, a number of terms are used. In order to provide a clear and consistent understanding of the specification and claims, including the scope to be given such terms, the following definitions are provided:

Backcross. The cross of a hybrid to either one of its parents. The offspring of such a cross is referred to as the backcross generation.

Backcross Method of Breeding. A system of breeding carried out by several generations of backcrossing to one of the parents of a hybrid and subsequent selection. The characteristics of the recurrent parent are retained for the most part, and characteristics from the nonrecurrent parent are added.

Bulk Method of Breeding. The growing of segregating generations of a hybrid of self-pollinating crops in a bulk, with or without mass selection, followed by individual plant selection in $F_6$ or later generations.

Cytoplasmic Inheritance. Transmission of hereditary characters through the cytoplasm as distinct from transmission by genes carried by chromosomes. Detected by differing contribution of male and female parents in reciprocal crosses.

Donor Parent. The parent from which one or a few genes are transferred to the recurrent parent in backcross breeding.

Ear Height. The ear height is a measure from the ground to the top developed ear node attachment and is measured in centimeters.

Early Stand Count. This is a measure of the stand establishment in the spring and represents the number of plants that emerge on a per-plot basis for the hybrid.

Elite. This term characterizes a plant or variety possessing favorable traits, such as, but not limited to, high yield, good grain quality and disease resistance.

Embryo. The rudimentary plant in a seed. The embryo arises from the zygote. In high oil corn breeding, increases in oil content are accompanied by increases in embryo size.

Endosperm. The nutritive tissue formed within the embryo sac in seed plants. It commonly arises following the fertilization of the two primary endosperm nuclei of the embryo sac by the two male sperms. In a diploid organism the endosperm is triploid.

Expressivity. The degree of manifestation of a genetic character.

$F_1$. The first generation of a cross.

$F_2$. The second filial generation obtained by self-fertilization or crossing inter se of $F_1$ individuals.

$F_3$. Progeny obtained by self-fertilizing $F_2$ individuals. Subsequent generations $F_4$, $F_5$, etc.

Field Corn. Varieties or cultivars of corn grown extensively on large acreage within a broad but defined geographic area for the production of grain and/or forage.

GDD Shed. The GDD is the number of growing degree days (GDD) or heat units required for an inbred line or hybrid to reach anthesis or pollen shed from the time of planting. Growing degree days are calculated by the Barger Method, where the heat units for a 24-hour period are:

$$GDD = \frac{(Max.+Min.)}{2} - 50$$

The highest maximum used is 86 degrees F. and the lowest minimum used is 50 degrees F. For each hybrid it takes a certain number of GDDs to reach various stages of plant development. GDDs are a way of measuring plant maturity.

General Combining Ability. The average or overall performance of a genetic strain in a series of crosses.

Genotype. The fundamental genetic constitution of an organism.

Germ. The embryo of the corn kernel. It contains most of the oil found in the kernel.

Grain. Comprises mature corn kernels produced by commercial growers for purposes other than growing or reproducing the species.

Grain Parent. Male sterile, elite hybrid that comprises a large majority of the plants in the TOPCROSS® grain production system.

Grain Parent Seed. Corn seed used to produce grain parent plants.

Grain Quality Trait. This is any attribute of grain that is of commercial value. Such traits relate to the intermediate or final use of grain and include but are limited to the quantity or quality of oil, protein, starch, pigmentation, and fiber found in corn grain. Such traits also encompass physical attributes of the grain itself, such as grain texture, size, or hardness, among others. Certain of these compositional or physical attributes of grain correlate with functional attributes as well which are of commercial importance, such as susceptibility to breakage and spoilage, among others.

Heterozygous. A genetic condition existing when different alleles reside at corresponding loci on homologous chromosomes.

High Oil Source. A population of corn plants containing high oil genes used for corn breeding.

Homozygous. A genetic condition existing when identical alleles reside at corresponding loci on homologous chromosomes.

Hybrid. (1) The progeny of a cross fertilization between parents belonging to different genotypes. (2) The first generation offspring of a cross between two individuals differing in one or more genes.

Hybrid Vigor. The phenomenon in which the cross of two stocks produce hybrids that show increased vigor-heterosis compared to the parent stocks.

Inbred. A substantially homozygous individual, variety or line.

Inbred Line. (1) A line produced by continued inbreeding. In plant breeding a nearly homozygous line usually originating by continued self-fertilization, accompanied by selection. (2) A relatively homozygous line produced by inbreeding and selection.

Kernel. The corn caryopsis comprising a mature embryo and endosperm which are products of double fertilization.

Line. A group of individuals from a common ancestry. A more narrowly defined group than a variety.

Male Sterility. A condition in which pollen is absent or non-functional in flowering plants.

MN RM. This represents the Minnesota Relative Maturity Rating (MN RM) for the hybrid and is based on the harvest moisture of the grain relative to a standard set of checks of previously determined MN RM rating. Regression analysis is used to compute this rating.

Moisture. The moisture is the actual percentage moisture of the grain at harvest.

Ovule. A structure consisting of female reproductive tissue surrounded by maternal tissue.

Pedigree. A record of the ancestry of an individual, family, or strain.

Pedigree Breeding. A system of breeding in which individual plants are selected in the segregating generations from a cross on the basis of their desirability and on the basis of a pedigree record.

Percent Oil. The oil concentration of a corn kernel expressed on a dry weight basis.

Percent Yield. The yield obtained for a hybrid in terms of percent of the mean for the experiments in which it was grown.

Phenotype. (1) Physical or external appearance of an organism as contrasted with its genetic constitution (=genotype). (2) A group of organisms with similar physical or external makeup. (3) The observed character of an individual without reference to its genetic nature.

Plant Height. This is a measure of the height of the hybrid from the ground to the tip of the tassel and is measured in centimeters. The data is given in percentage of mean of the experiments in which the hybrid was grown.

Polar Nuclei. Found in the ovule to give rise to the embryo and endosperm of the mature corn kernel.

Pollen. A structure which contains the two haploid sperm nuclei which fuse with the egg nucleus and polar nuclei found in the ovule to give rise to the embryo and endosperm of the mature corn kernel.

Pollinators. Male fertile corn plants that are used to pollinate male sterile hybrid corn plants.

Pollinator Seed. Corn seed that, when sown, germinates to produce pollinator plants.

Population. In genetics, a community of individuals which share a common gene pool. In statistics, a hypothetical and infinitely large series of potential observations among which observations actually made constitute a sample.

Recurrent Parent. Used in backcrosses to refer to the parent to which the first cross and successive backcrossed plants are crossed.

Seed. Mature corn kernels produced for the purpose of propagating the species.

Seed parent. A corn line that is pollinated by pollen from pollinator plants, with hybrid corn seed resulting from this pollination.

Seedling Vigor. This is the visual rating (1 to 5) of the amount of vegetative growth after emergence at the seedling stage (approximately five leaves). A higher score indicates better vigor.

Stay Green. Stay green is the measure of plant health near the time of black layer formation (physiological maturity). A low score on a scale of 1 to 5 indicates better late-season plant health.

Synthetic Hybrid. Any offspring of a cross between two genetically unlike synthetic individuals or unlike individuals.

Synthetic Population. A genetically heterogeneous collection of plants of known ancestry created by the intermating of any combination of inbreds, hybrids, varieties, populations, races or synthetics.

Synthetic Variety. A variety produced by crossing inter se a number of genotypes selected for good combining ability in all possible hybrid combinations, with subsequent maintenance of the variety by open pollination.

Test Cross. A cross of a double or multiple heterozygote to the corresponding multiple recessive to test for homozygosity or linkage.

Test Weight. The measure of the weight of the grain in pounds for a given volume (eg. bushel), adjusted for percent moisture.

TC BLEND®. A trademark of E.I. du Pont de Nemours and Company for corn seed for agricultural purposes.

TOPCROSS®. A trademark of E.I. du Pont de Nemours and Company for high oil corn seed.

TOPCROSS® Grain Production System. A method of commercial corn production whereby a low yielding male fertile corn pollinator is blended at 8 to 20 percent of the total seed count with an elite high yielding male sterile hybrid grain parent and allowed to pollinate the male sterile grain parent to produce grain having increased food and feed nutritional value, thus capitalizing on the high yield potential of the male sterile hybrid grain parent while contributing the grain quality traits from the fertile pollinator.

Variety. A subdivision of a species. A group of individuals within a species which are distinct in form or function from other similar arrays of individuals.

Yield (Bushels/Acre). The yield in bushels/acre is the actual yield of the grain at harvest adjusted to 15.5% moisture.

DETAILED DESCRIPTION OF THE INVENTION

P129-wx is a yellow dent corn, high oil single cross synthetic hybrid having superior agronomic characteristics and the ability to impart desirable grain quality traits to a first generation grain when used as a pollinator in the TOPCROSS® grain production system.

Synthetic hybrid P129-wx is produced by planting synthetic populations P129A-wx and P129B-wx, allowing one synthetic to pollinate the other, and harvesting the resulting seed. Either synthetic parental population may be used as female parent or male parent. Preferably, synthetic P129B-wx is the female of the cross and synthetic P129A-wx is the male of the cross because of the larger seed size grade-out resulting from the P129B-wx seed parent in hybrid synthetic production. Production planting of the male and female synthetics can be made at the same time due to the fact that male pollen is shed at the same time the female silks are receptive to the pollen.

P129A-wx and P129B-wx were produced by conducting a series of crosses, selfings and backcrosses beginning in 1994 at Applicant's El Paso, Ill. nursery with the crossing of P39.1A to A632-wx and P39.1B to Mo17-wx and subsequently backcrossing to the respective A and B parental lines for three consecutive generations followed by three continuous generations of random mating and selection within the A or B populations accompanied by ear-to-row test crosses to a wx-hybrid tester to identify homozygous waxy gene and high oil segregants.

The procedure for producing the P129-wx synthetic hybrid with A-Reid-wx and B-Lancaster-wx conversion populations for an early generation testing series was as follows. Approximately 1,000 plants from the Reid and Lancaster heterotic groups that were sib-pollinated and test-crossed to Pfister Hybrid X571-wx in summer of 1997 were analyzed for oil percentage. Approximately 900 plants from the initial backcross populations to P39A and P39B cytoplasm were discarded from the original 1,000 plants at harvest on the basis of vigor, disease and insect susceptibility, ear and kernel type, oil content and other characteristics. The mean grain oil content was fixed at 7.5 to 8.0% oil in the sibs recovered from the backcross populations to P39 parental populations.

The ten families from each heterotic group expressing the highest oil percentage and best phenotype were used as parental material for a diallel mating series to produce three separate early testing populations: A-Reid-wx, B-Lancaster-wx and A-Reid-wx×B-Lancaster-wx to produce an early generation P129-wx hybrid population for early generation tests in 1998 to evaluate the success of recovery of favorable dominant oil gene linkage groups.

In the first cycle of the early generation testing series of P129A-wx and P129B-wx, equal quantities of seed of each of the 45 diallel crosses within each heterotic population were bulked and the composite seed was used to plant isolation plots of approximately 20,000 plants which were random mated to establish the P129A-wx and P129B-wx synthetics as separate populations. The composite seed of the A-Reid-wx×B-lancaster-wx diallel was also bulked to test P129-wx blends with male sterility waxy hybrids for early generation yield trials for evaluation of the recovery of the favorable dominant oil gene linkage groups.

When produced according to the method disclosed herein, both P129A-wx and P129B-wx breed true, that is, produce a P129-wx synthetic hybrid that is both reproducible and usable as a high oil pollinator in the TOPCROSS® grain production system.

CHARACTERISTICS OF P129-wx

Synthetic corn hybrid P129-wx most closely resembles maize synthetics ASKC28, ASKC20 and UHO in characteristics of plant type, ear type, kernel type and usage, but P129-wx is considerably earlier in maturity and expresses moderately higher grain test weight with normal grain and dent phenotype that expresses a moderately soft starch with waxy grain phenotype.

P129-wx synthetic hybrid has the following characteristics, based on data primarily collected at Applicant's El Paso, Ill. research facility (numerical values given are averages taken across a fifty plant sample):

TABLE 1

SYNTHETIC HYBRID P129-wx DESCRIPTION INFORMATION

| | |
|---|---|
| Type: | Dent/High Oil |
| Region Best Adapted: | Most Northern, Central, and Northeastern Regions of USA Cornbelt |
| A. Maturity: | Zone 1-2 |
| Synthetic Maize Hybrid: | P129-wx |
| Heat Units from Emergence to Shed: | 1019 GDD (1998) |
| Heat Units from Emergence to Silk: | 1082 GDD (1998) |
| Heat Units from 50% Silk to 25% Kernel Moisture: | 1447 GDD (1998) |
| Heat Units from Emergence to 25% Kernel Moisture: | 2506 GDD (1998) |
| No. Reps.: | 8 |

TABLE 1-continued

SYNTHETIC HYBRID P129-wx DESCRIPTION INFORMATION

Where Heat Units* = [(Max. Temp. (<86 Degrees F.) + Min. Temp. (>50 Degrees F.))/2] − 50
*If Max. Temp. is greater than 86 degrees Fahrenheit, then 86 is used and if Min. Temp. is less than 50, then 50 is used. Heat units accumulated daily and can not be less than 0.

B. Plant Characteristics:

| | |
|---|---|
| Height (to tassel tip): | 191 cm |
| Length of Top Ear Internode: | 15 cm |
| Number of Ears per Stalk: | Slight two-ear tendency |
| Ear Height (to base of top ear): | 45 cm |
| Number of Tillers: | Mostly none, occasional one |
| Cytoplasm Type: | Normal |
| Brace Root Color: | Green with few purple |
| Number of Brace Root Nodes: | Slight two-node tendency |
| Number of Brace Roots: | 16 |
| Stalk: | Straight |

C. Leaf:

| | |
|---|---|
| Color: | Green |
| Stalk Color: | Green |
| Angle from Stalk: | 51 Degrees |
| Attitude of Blade: | Slightly curved |
| Marginal Waves (number): | 2 |
| Number of Leaves (mature plants): | 11 |
| Sheath Pubescence: | Smooth, segregating for smooth and pubescence |
| Color of Sheath: | Pale green |
| Longitudinal Creases: | Absent |
| Length (Ear node leaf): | 70 cm |
| Width (widest point, ear node leaf): | 9 cm |
| Coleoptile Sheath Color: | Mostly green with a few purple |
| First Leaf, Shape of Tip | Round |

D. Tassel:

| | |
|---|---|
| Attitude of Lateral Branches: | Mostly straight, segregating for curved |
| Number Lateral Branches: | 14 |
| Length of Lateral Branches: | 23 cm |
| Branch Angle from Central Spike: | 49 degrees |
| Length of Main Axis Above Lowest Branch: | 39 cm |
| Length (from flag leaf): | 49 cm |
| Peduncle Length (flag leaf to basal branches): | 10 cm |
| Anther Color: | Yellow |
| Glume Color: | Green |
| Density of Spikelets: | Medium |

E. Ear (Husked Ear Data Except When Stated Otherwise):

| | |
|---|---|
| Length: | 17 cm |
| Weight (dried to 15.5% grain moisture): | 141 gm |
| Mid-point Diameter: | 4 cm |
| Silk Color (at silking): | Pale green |
| Husk Extension (Harvest stage): | Short, 4 cm (ear tip occasionally exposed) |
| Husk Leaf (number): | 7 |
| Husk Leaf Length: | 4 cm |
| Number of Husks: | 12 |
| Taper of Ear: | Average taper |
| Position at Dry Husk Stage: | Upright |
| Kernel Rows: | 18; Distinct, straight |
| Husk Color (fresh): | Light green |
| Husk Color (dry): | Buff |
| Shank Length: | 25 cm long |
| Shank (No. of internodes): | 10 |
| Drying Time (unhusked ear): | Average |
| Husk Length: | 28 cm |
| Husk Width: | 16 cm |
| Husk Area: | 466 cm$^2$ |

F. Kernel (dried, size from ear mid-point):

| | |
|---|---|
| Length: | 10 mm |
| Width: | 6 mm |
| Thickness: | 4 mm |
| Shape Grade (% rounds): | 34%(±3%) based on parent test |
| Type of Grain in Middle of Ear (Dent vs Flint): | Dent |
| Pericarp Color: | Colorless |
| Aleurone Color: | Homozygous; yellow |
| Cap Color: | Yellow |
| Endosperm Color: | Yellow |
| Color of Grain on Dorsal Side: | Yellow |
| Endosperm Starch Type: | Amylopectin, waxy starch (homozygous for wx-gene) |
| Gm Wt/100 Seeds (unsized): | 19 gm |
| Test Weight: | 59 lbs./bu. |
| Percent Oil: | 16.74 percent (1998) |
| Percent Protein: | 12.80 percent (1998) |
| Percent Starch: | 51 percent (1998) |
| Density: | 1.19 gm/ml (1998) |

G. Cob (dried, size from ear mid-point):

| | |
|---|---|
| Diameter at mid-point: | 27 mm |
| Strength: | Strong |
| Color: | Red, segregating for white and red cob color but was heterozygous for red. |

H. Diseases:

| | |
|---|---|
| Northern Leaf Blight: | Intermediate |
| Goss's Bacterial Wilt: | Intermediate |
| Southern Corn Leaf Blight: | Susceptible |
| Heat Smut: | Susceptible |
| Common Smut: | Resistant |
| Stewart's Bacterial Wilt: | Intermediate |
| Corn Lethal Necrosis: | Susceptible |
| Northern Leaf Spot: | Intermediate |
| Common Northern Rust: | Intermediate |
| Southern Rust: | Susceptible |
| Eye Spot: | Intermediate |
| Gray Leaf Spot: | Susceptible |
| Fusarium Ear Rot: | Resistant |
| Fusarium Stalk Rot: | Intermediate |
| Diplodia Ear Rot: | Susceptible |
| Diplodia Stalk Rot: | Intermediate |
| MDMV: | Susceptible |
| Stunt: | Susceptible |
| Stay Green: | Intermediate |

I. Insects:

| | |
|---|---|
| European Corn Borer: | Susceptible |

J. Variety most closely resembling P129-wx:

| Character | Synthetic Hybrid, Hybrid, and/or Inbred |
|---|---|
| Maturity | P53, P39, Pfister Hybrid 1571 |
| Plant Type | ASKC28, UHO, ASKC20, P39 |
| Ear Type | ASKC28, UHO, ASKC20, P53 |
| Kernel Type | UHO, ASKC20, ASKC28 |
| Usage | ASKC28, UHO, ASKC20 |

P129-wx is adapted over a wide area of the northern corn belt and can be used advantageously as a pollinator in seed blends with male sterile hybrids from approximately 95–100 relative maturity based on the Minnesota Relative Maturity Rating System for harvest moisture of the grain. P129-wx cold test vigor was excellent in laboratory tests, exhibiting 92% emergence compared to 90% emergence for ASKC20, 92% emergence for UHOC3, and 83% emergence for ASKC28. Kernel size-out is also very good for P129-wx, with approximately 66% of the kernels falling in the medium flat category.

Although P129-wx's primary use would be as a pollinator in the TOPCROSS® grain production system with blends of early maturing corn hybrid male sterile grain parents, P129-wx is also an acceptable male to be crossed to later maturing full season high oil pollinators to develop medium maturity pollinators for expanding the use of its genetics to fuller season maturity grain parents.

Pollen production is good with P129-wx. Under extreme heat and drought stress, P129-wx may top fire and have some tassel blasting (necrosis of top leaves and tassel, respectively). P129-wx sheds pollen for approximately twenty days (Table 3) and should be blended in sufficient concentrations (at approximately 8–10% pollinator seed to 90–92% male sterile hybrid grain parent seed) to ensure adequate pollen in commercial production of high oil corn grain where it is used as a male pollinator.

As a pollinator, P129-wx has shown uniformity and stability within the limits of environmental influence for the grain traits of yield, moisture, oil concentration, protein concentration and test weight as shown in Table 2. P129-wx has expressed segregation for red and white cob color because of the genetic differences of P129A-wx and P129B-wx synthetic parental populations. P129-wx is a synthetic hybrid that has been maintained by hand and cross pollination in isolated fields with continued observation of high oil for uniformity of dominant high oil genetics. Although segregating for cob color, glume color and plant height in test crosses, P129-wx synthetic has consistently expressed high oil across different environments.

P129-wx is an early maturity flowering synthetic hybrid, broadly adapted to the corn growing areas of the Northern United States and Southern Canada. P129-wx has expressed high oil and excellent cold soil seedling vigor that conditions low grain moisture in the grain of male sterile hybrid grain parents.

BENEFITS OF P129-wx AS A POLLINATOR

In field tests of the TOPCROSS® grain production system using P129-wx as the pollinator and a male sterile hybrid grain parent, P129-wx was found to induce superior grain quality characteristics in grain arising on the male sterile hybrid.

In field tests, P129-wx and male sterile grain parent plants were allowed to grow unmolested to maturity. Both varieties were allowed to continue to grow and natural cross-pollination was allowed to occur by the action of the wind as is normal with most grasses, including corn. Of course, only pollen from the fertile male parent, P129-wx, was available for pollination of the male sterile hybrid grain parent; the tassels, or flower bearing parts, of the grain parent having been rendered sterile by genetic/cytoplasmic mechanisms. For convenience, the grain harvested from the male sterile grain parent plants and the P129-wx plants will hereinafter be referred to as "high oil corn grain."

The fields where high oil corn grain was produced were well isolated from other corn fields to prevent any accidental contamination with ambient pollen. Such isolation techniques may be accomplished by timed delay with other hybrid corn production fields or by using a space distance pattern of more than 70 m from normal corn, well known to those skilled in the art of the seed corn industry.

Both the male fertile pollinator and male sterile hybrid grain parent varieties comprising the corn seed blend were allowed to continue to grow and be harvested. The ears harvested from the male sterile grain parent expressed the higher grain yield potential of the elite male sterile grain parent and the high oil, protein and grain density qualities of the pollen parent. The grain from the male parent synthetic variety ears may be harvested along with the grain of the male sterile grain parent hybrid for high oil corn use.

Because the same oil source (i.e. ASKC28) was used in the development of the P129A-wx-Reid and P129B-wx-Lancaster parental populations, only modest heterotic effects for yield were expressed in P129-wx. The low grain yields expected from synthetic hybrid P129-wx pollinator dictated the need for a low percent of pollinator in the pollinator-grain parent seed blend so as to maximize yield, but a high enough percent was needed to ensure sufficient pollination of the elite male sterile grain parent hybrid.

EXAMPLES OF USING P129-wx AS A POLLINATOR

In the examples that follow, the characteristics of high oil corn grain produced using P129-wx as a pollinator are provided.

1998 Strip Test Trials

First year (1998) strip tests trials were conducted at El Paso, Ill., and Fremont, Wis. comparing the characteristics of grain from various hybrids rendered male sterile and pollinated by P129-wx with characteristics of grain produced from grow outs of the same hybrids in their fertile state ("Hybrid Self"). The hybrids used were Pfister Hybrids 1571 and X571 and Brown Seed Hybrids 5041-VPWX, 6791-VPWX and 5291-VPWX. The results are presented in Table 2.

TABLE 2

1998 P129-wx Strip Tests Results - El Paso, Illinois and Fremont, Wisconsin

| | Grain Yield (Bu/A.) | | | Moisture Percent | | | Oil Percent | | | Protein Percent | | | Test Weight (Lbs./Bu.) | | |
|---|---|---|---|---|---|---|---|---|---|---|---|---|---|---|---|
| Hybrid Grain Parent | Top-Cross | % of GP | Hybrid GP Self | Top-Cross | % of GP | Hybrid GP Self | Top-Cross | % of GP | Hybrid GP Self | Top-Cross | % of GP | Hybrid GP Self | Top-Cross | % of GP | Hybrid GP Self |
| El Paso, Illinois | | | | | | | | | | | | | | | |
| Pfister Hybrid X571-wx | 150.4 | 103 | 145.6 | 11.7 | 85 | 13.7 | 7.77 | 186 | 4.18 | 9.1 | 99 | 9.2 | 59.5 | 103 | 57.8 |
| Pfister Hybrid 1571-wx | 147.7 | 98 | 150.4 | 18.4 | 131 | 14.0 | 8.43 | 194 | 4.34 | 10.0 | 114 | 8.8 | 60.4 | 104 | 58.2 |

TABLE 2-continued

1998 P129-wx Strip Tests Results - El Paso, Illinois and Fremont, Wisconsin

| Hybrid Grain Parent | Grain Yield (Bu/A.) | | | Moisture Percent | | | Oil Percent | | | Protein Percent | | | Test Weight (Lbs./Bu.) | | |
|---|---|---|---|---|---|---|---|---|---|---|---|---|---|---|---|
| | Top-Cross | % of GP | Hybrid GP Self | Top-Cross | % of GP | Hybrid GP Self | Top-Cross | % of GP | Hybrid GP Self | Top-Cross | % of GP | Hybrid GP Self | Top-Cross | % of GP | Hybrid GP Self |
| Fremont, Wisconsin | | | | | | | | | | | | | | | |
| Brown Hybrid 5091-VPWX | | | 145.6 | 12.5 | 91 | 13.7 | 8.31 | 201 | 4.18 | 10.0 | 95 | 9.2 | 59.4 | 103 | 57.8 |
| Brown Hybrid 6791-VPWX | | | 150.4 | 13.1 | 94 | 14.0 | 5.94 | 177 | 4.34 | 10.5 | 97 | 8.8 | 60.3 | 104 | 58.2 |
| Brown Hybrid 5291-VPWX | | | 148.6 | 13.1 | 87 | 15.0 | 7.43 | 153 | 4.51 | 11.7 | 77 | 8.7 | 59.8 | 105 | 56.8 |
| Overall Mean | 149.1 | 100 | 148.1 | 13.8 | 98 | 14.1 | 7.80 | 182 | 4.31 | 8.6 | 96 | 8.9 | 59.9 | 104 | 57.8 |

NOTE: "TopCross" as used in this table refers to grain resulting from the pollination by P129-wx of both the male sterile hybrid grain parent and P129-wx.

Traits obtained from the strip test include the following:

"Grain yield", expressed in bushels per acre for both the grain produced by the pollination of the male sterile grain parent hybrid by P129-wx and the grain produced from the grow out of the fertile hybrid.

"Moisture Percent", expressed as a percentage of total kernel weight for both grain produced from the pollination of the male sterile hybrid by P129-wx and for the grow out of the fertile hybrid. Moisture percent was determined by distillation on a Brown-Duvel moisture tester manufactured by the Seed Trade Reporting Bureau of Chicago, Ill. Electronic moisture testers were calibrated against the moisture determinations of the Brown-Duvel moisture tester in field harvest tests.

"Oil Percent", expressed as a percentage of the total kernel dry weight for both grain produced from the pollination of the male sterile hybrid by P129-wx and for the grow out of the fertile hybrid. Thus oil percent is a measure of the content of oil in grain at harvest. Oil percent was determined by NIR on a dry matter basis (0% moisture).

"Protein Percent", expressed as a percentage of protein in the grain on a dry matter basis as determined by NIR for both grain produced from the pollination of the male sterile hybrid by P129-wx and for the grow out of the fertile hybrid.

"Test Weight", expressed as the weight of the grain in pounds for a given volume (bushel) adjusted for percent moisture for both grain produced from the pollination of the male sterile hybrid by P129-wx and for the grow out of the fertile hybrid.

Grain Yield Comparisons—High Oil Corn Grain Versus Hybrid Self

In the 1998 strip test trials (Table 2), blends of 8–9% pollinator seed and 91–92 percent male sterile hybrid seed were planted and grown to maturity. Grain from both the male sterile hybrid plants i.e., high oil corn and the pollinator plants was harvested.

As shown in Table 2, the overall mean yield of grain produced by the pollination of the male sterile hybrids by P129-wx during the first year (1998) strip tests was 100% of the overall mean yield of grain produced from the fertile grain parent grow outs in eleven comparisons.

Moisture Comparisons—High Oil Corn Grain Versus Hybrid Self

Conventional high oil hybrids traditionally express higher grain moisture at harvest and are slower to dry down than lower-oil dent hybrids of the same maturity. To test this concept of higher moisture associated with higher oil content of grain, comparisons were made of moisture at harvest of grain resulting from the pollination by P129-wx of the male sterile hybrids and grain resulting from the self pollination of the comparable fertile hybrids.

In the first year (1998) trials (Table 2), the overall mean grain moisture at harvest from the sterile grain parent hybrids pollinated by P129-wx was not significantly different than the grain moisture from the fertile grain parent hybrids alone in the hybrid grain parent comparisons. Since higher oil content resulted in no significant moisture differences in these comparisons, the first year data did not support the conventional theory regarding the relationship between oil content and grain moisture.

Oil Comparisons—High Oil Corn Grain Versus Hybrid Self

In the first year (1998) strip tests made at El Paso, Ill., and Fremont, Wis., the oil contents of grain produced from the pollination by P129-wx of the male sterile hybrids were compared to grain produced from the self pollination of the comparable fertile hybrids. The results, shown in Table 2, show a consistent increase in oil percent in the high oil corn grain compared to the hybrid selfs. To take but two examples, there was about a 194% increase in oil when Pfister Hybrid 1571-wx was pollinated by P129-wx (8.43% versus 4.34%), and about a 186% increase in oil when Pfister Hybrid X571-wx was pollinated by P129-wx (7.77% versus 4.18%).

Protein Comparisons—High Oil Corn Grain Versus Hybrid Self

In first year (1998) strip tests (Table 2), protein content of the grain resulting from the pollination of the male sterile hybrid by P129-wx was compared to the protein content of grain produced from open pollinated fertile hybrid checks. Analysis of population means indicated that P129-wx did not significantly increase protein in the TOPCROSS® grain compared to the grain from the fertile grain parent check. The fact that the high oil corn grain did not exhibit higher protein than that of the fertile grain parent hybrid may have been due to a lower level of nitrogen in the field.

Test Weight Comparisons—High Oil Corn Grain Versus Hybrid Self

Test weight of grain is a function of kernel density. In first year strip tests, comparisons were made of the test weight of high oil corn grain resulting from the pollination by P129- wx of male sterile hybrids against the test weight of grain resulting from the self pollination of the comparable fertile hybrids. As shown in Table 2, the overall mean test weight of high oil corn grain was 59.9 Lbs./Bu., or 104% of the mean test weight of the selfed hybrids (57.8 Lbs./Bu.).

P129-wx conditions a slight increase in test weight in the high oil corn grain which may result in a slight yield advantage.

Tassel-Silk Synchronization—P129-wx Pollen Shed and Grain Parent Silk Extrusion

The success of the TOPCROSS® grain production system is dependent on the synchronization of pollen shed from the pollinator with the extrusion of silks from the male sterile grain parent hybrid, which is termed nicking.

Table 3 presents results of tassel-silk date observations and growing degree days (GDD) to tassel shed and silk flowering for P129-wx pollinator and Pfister Hybrid X571-wx, respectively. As shown in the table, in 1998 strip tests the pollination period of P129-wx began July 5 and ended July 24, a twenty (20) day period. Peak pollination, i.e., the date during which 50% pollen shedding was achieved, occurred on July 11 which resulted from an accumulation of 1019 GDD. By comparison, the peak silk extrusion date for Pfister Hybrid X571-wx was slightly later—July 14—which resulted from an accumulation of 1082 GDD. These data indicate that the nicking of pollinator P129-wx with male sterile Pfister Hybrid X571-wx is acceptable for commercial high oil corn grain production.

Comparisons of Oil, Protein and Moisture in Grain Produced from Hybrids Pollinated by P129-wx and Self Pollinated Fertile Hybrids Harvested Over Time Table 4 presents the oil content, protein content and moisture of grain produced from Pfister Hybrids X571-wx and X571-Sdms (columns one and two), grain produced from Pfister Hybrids X571-wx and X571-wx-Sdms pollinated by P129-wx (columns three and four), and grain produced from self-pollinated P129-wx (column five) when the grain was harvested 35 days after flowering and then harvested on selected days to and beyond the onset of physiological maturity (i.e., black-layer).

Pfister Hybrid X571-wx-Sdms pollinated by P129-wx expressed 6.9% oil content of the grain as early as 761.5 GDD after flowering, thus indicating a very high level of oil while the plant foliage was green and actively growing. This permits an early harvest for silage and/or earlage while maintaining a high energy recovery from the grain.

A comparison of the protein content data for Pfister Hybrid X571-wx-Sdms pollinated by P129-wx shows little difference in protein at 35 days after flowering through 75 days, suggesting the physiological make-up of the seed is basically complete at the early harvest date.

A comparison of moisture over the course of 40 days (i.e., August 17 to September 21) illustrates the rate of dry down. The moisture data indicate there was a slight increase of 1.3 absolute percent in the mean value of grain moisture between grain resulting from the self-pollination of fertile hybrid X571-wx (column one) and grain resulting from the pollination by P129-wx of male sterile hybrid X571-wx-Sdms (column four). However, the rate of dry down of grain arising on self-pollinated P129-wx (column five) was sub-

TABLE 3

Comparison of the Tassel Shedding Period for P129-wx with the Silk Extrusion Period for Pfister Hybrid X571-wx
Total Plants Observed - 100
1998 Field Test Data

| Date | July 5 | July 6 | July 7 | July 8 | July 9 | July 10 | July 11 | July 12 | July 13 | July 14 |
|---|---|---|---|---|---|---|---|---|---|---|
| Percent of Pollinator P129-wx to Start Shedding | 1 | 1 | 3 | 1 | 15 | 25 | 18 | 8 | 9 | 7 |
| Percent of Pollinator P129-wx to Stop Shedding | | | | | | | | | | 2 |
| Percent of Hybrid X571-wx to Begin Silk Extrusion | | | 2 | 4 | 3 | 3 | 6 | 5 | 9 | 20 |
| Growing Degree Days | 881 | 905 | 929 | 953 | 977 | 1000 | 1019 | 1036 | 1058 | 1082 |

| Date | July 15 | July 16 | July 17 | July 18 | July 19 | July 20 | July 21 | July 22 | July 23 | July 24 |
|---|---|---|---|---|---|---|---|---|---|---|
| Percent of Pollinator P129-wx to Start Shedding | 4 | 4 | | 1 | 1 | 1 | 1 | | | |
| Percent of Pollinator P129-wx to Stop Shedding | 4 | 18 | 41 | 14 | 1 | 6 | 7 | 4 | 1 | 2 |
| Percent of Hybrid X571-wx to Begin Silk Extrusion | 13 | 6 | 9 | 4 | 2 | 12 | 1 | 1 | | |
| Growing Degree Days | 1103 | 1128 | 1150 | 1174 | 1202 | 1226 | 1255 | 1276 | 1297 | 1313 | stantially slower than the rate of dry down of grain from the self-pollinated hybrid (columns one and two) or the hybrid pollinated by P129-wx (columns three and four).

was also much higher in the silage from the P129-wx pollination, indicating an increase in the productivity per acre for each cow.

TABLE 4

Percent Oil, Protein and Moisture of Grain at Harvest Across Days Commencing 35 Days After Pollination Through 75 Days After Pollination of Five Corn Types (1998)

| Column-> Type(s) Planted-> | | (1) Pfister X571-wx | | | (2) Pfister X571-wx-Sdms (Sib) | | | (3) Pfister X571-wx and P129-wx | | | (4) Pfister X571-wx-Sdms and P129-wx | | | (5) P129- wx | | | GDD from Flowering |
|---|---|---|---|---|---|---|---|---|---|---|---|---|---|---|---|---|---|
| (A) | (B) | Oil | Protein | Moist | Oil | Protein | Moist | Oil | Protein | Moist | Oil | Protein | Moist | Oil | Protein | Moist | to Harvest |
| 8/17 | (35) | 4.2 | 11.0 | 47.6 | 4.6 | 10.2 | 47.8 | 7.4 | 11.8 | 49.8 | 6.9 | 13.1 | 49.8 | 13.6 | 12.6 | 46.5 | 761.5 |
| 8/21 | (39) | 4.8 | 9.0 | 43.9 | 4.5 | 10.0 | 42.9 | 7.5 | 12.5 | 43.5 | 7.6 | 12.1 | 45.3 | 13.2 | 12.6 | 42.7 | 844.0 |
| 8/26 | (44) | 4.0 | 11.2 | 36.1 | 4.4 | 10.3 | 35.0 | 8.0 | 12.6 | 37.3 | 7.8 | 12.0 | 38.9 | 15.4 | 12.2 | 36.5 | 973.0 |
| 8/31 | (49) | 4.0 | 12.1 | 32.6 | 4.4 | 10.3 | 31.5 | 7.3 | 13.8 | 28.8 | 8.0 | 11.5 | 33.8 | 15.3 | 12.3 | 34.7 | 1076.0 |
| 9/4 | (53) | 4.4 | 10.6 | 29.0* | 4.2 | 10.1 | 28.0* | 7.6 | 12.5 | 26.7* | 8.0 | 11.3 | 28.6* | 15.4 | 11.6 | 30.4* | 1156.0 |
| 9/10 | (59) | 4.4 | 9.1 | 19.4 | 4.1 | 11.9 | 19.2 | 7.6 | 12.4 | 19.2 | 8.1 | 12.4 | 22.9 | 13.8 | 12.9 | 27.8 | 1265.5 |
| 9/15 | (64) | 4.1 | 9.5 | 17.7 | 4.5 | 9.4 | 14.1 | 7.9 | 12.0 | 13.7 | 7.8 | 12.2 | 15.4 | 13.1 | 14.0 | 28.5 | 1364.0 |
| 9/19 | (68) | | | | | | | | | | | | | | | 25.3 | 1447.0 |
| 9/21 | (75) | 3.8 | 11.7 | 12.2 | 4.0 | 10.5 | 15.6 | 7.8 | 12.7 | 13.7 | 8.3 | 12.5 | 13.9 | 14.9 | 13.6 | 23.6 | 1489.0 |
| MEAN | | 4.2 | 10.5 | 29.8 | 4.3 | 10.3 | 29.3 | 7.6 | 12.5 | 29.1 | 7.8 | 12.1 | 31.1 | 14.3 | 12.8 | 32.9 | 1153.0 |

(A) = Harvest Date
(B) = Days After Pollination
*Date of black layer, physiological maturity.

Silage

When P129-wx was used to pollinate elite male sterile grain parent hybrids, P129-wx conditioned the expression of a waxy starch phenotype with normal test weight of grain. When the grain parent hybrids and P129-wx are harvested as whole plants, the grain parent plants combined with the pollinator plants make excellent silage.

Nutritional values of silage from Pfister Hybrids X571-wx-Sdms, 1571-wx-Sdms and Brown Seed Hybrids 5041-wx-Sdms, 5291-wx-Sdms and 6791-wx-Sdms pollinated by P129-wx compared to silage from the normal fertile grain parent type hybrids, X571-wx, 1571-wx, 5041-wx, 5291-wx and 6791-wx are presented in Table 5 from five silage experiments. Silage nutritional evaluations were provided by Optimum Quality Grains Laboratory, Des Moines, Iowa.

In the first experiment, nutritional values of silage were compared to silage from the pollination by P129-wx of the male sterile grain parent and P129-wx from the fertile normal grain parent alone. Corn silage resulting from the P129-wx pollination provided greater total digestible nutrients (TDN) (68.3% versus 66.8%) and greater net energy for lactation (NEL) (0.70 MCal/lb. versus 0.69 MCal/lb.). Higher NEL and TDN permits greater flexibility in animal feed formulations and increases the productivity per acre for each cow. Protein content of silage from the P129-wx pollination was about one percent higher on an absolute basis than silage produced from self-pollinated fertile hybrid X571-wx (8.41% versus 7.46%). Fat content, a function of oil content, was 0.93% higher on an absolute basis in the silage from the P129-wx pollination.

In experiments 2, 3, 4 and 5 with Pfister Hybrid 1571-wx and Brown Hybrids 5041-wx, 5291-wx and 6791-wx, the results were similar. NEL, TDL and protein values for the silage from the P129-wx pollination, were higher than those for the self-pollinated hybrids in every case. As expected, fat

TABLE 5

Silage Evaluation-Percent Dry Weight Basis (1998)

| Hybrid | Protein % | Fat % | NEL* MCal/lb. | TDN* % |
|---|---|---|---|---|
| Experiment 1 | | | | |
| Pfister X571-wx-Sdms + P129-wx | 8.41 | 4.16 | 0.70 | 68.3 |
| Pfister X571-wx | 7.46 | 3.23 | 0.69 | 66.8 |
| Experiment 2 | | | | |
| Pfister 1571-wx-Sdms + P129-wx | 9.28 | 4.23 | 0.71 | 68.1 |
| Pfister 1571-wx | 7.42 | 3.28 | 0.69 | 67.3 |
| Experiment 3 | | | | |
| Brown 5041VPWX-Sdms + P129-wx | 8.87 | 6.02 | 0.74 | 70.8 |
| Brown 5041-wx | 7.46 | 3.23 | 0.69 | 66.8 |
| Experiment 4 | | | | |
| Brown 5291VPWX-Sdms + P129-wx | 10.02 | 5.22 | 0.71 | 68.1 |
| Brown 5291-wx | 7.42 | 3.28 | 0.69 | 67.3 |
| Experiment 5 | | | | |
| Brown 6791VPWX-Sdms + P129-wx | 9.12 | 4.92 | 0.72 | 69.7 |
| Brown 6791-wx | 7.40 | 2.35 | 0.69 | 67.6 |

*NEL = Net energy for lactation. TDN = Total Digestible Nutrients.
Protein, fat and TDN expressed as percent of dry matter.

DEPOSIT INFORMATION

Applicant has made available to the public without restriction a deposit of at least 2500 seeds of synthetic hybrid P129-wx, at least 2500 seeds of P129A-wx-Reid, and at least 2500 seeds of P129B-wx-Lancaster with the American Type Culture Collection (ATCC), Rockville, Md. 20852. The depositor was Optimum Quality Grains, L.L.C. The date of the deposit was Jun. 4, 1999. P129-wx was assigned Deposit No. PTA-177. P129A-wx was assigned Deposit No. PTA-178. P129B-wx was assigned Deposit No. PTA-179. The viability of the seeds was tested on Jun. 14, 1999. On this date, the seeds were viable and capable of reproduction.

The seeds deposited with the ATCC were taken from the same deposits maintained by Optimum Quality Grains, L.L.C., Box 19, 90 North Fayette Street, El Paso, Ill. 61738, since prior to the filing date of this application. The deposits will be maintained in the ATCC depository, which is a public depository, for a period of 30 years, or 5 years after the most recent request, or for the enforceable life of the patent, whichever is longer, and will be replaced if they become nonviable during that period.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed is:

1. A synthetic hybrid corn seed designated P129-wx, a representative sample of which has been deposited with the ATCC under Deposit No. PTA-177.

2. A synthetic hybrid corn plant or its parts produced by the seed of claim 1.

3. Pollen of the synthetic hybrid corn plant of claim 2.

4. A tissue culture comprising regenerable cells of the synthetic hybrid corn plant of claim 2.

5. A corn plant regenerated from the tissue culture of claim 4, wherein said plant has all the physiological and morphological characteristics of P129-wx.

6. A synthetic hybrid corn plant having all the essential physiological and morphological characteristics of the synthetic hybrid corn plant P129-wx, Deposit No. PTA-177.

7. A method for producing a synthetic hybrid corn seed designated P129-wx, Deposit No. PTA-177, comprising the steps of:
   a) planting in pollinating proximity seeds of corn synthetic lines P129A-wx, ATCC Accession No. PTA-178, and P129B-wx, Deposit No. PTA-179;
   b) cultivating corn plants resulting from the planting until the time of flowering;
   c) emasculating the flowers of the plants of either synthetic line P129A-wx or P129B-wx;
   d) allowing natural cross pollination to occur between the synthetic lines; and
   e) harvesting seeds produced on the emasculated plants of the synthetic line.

8. A synthetic hybrid corn plant produced by crossing P129-wx, Deposit No. PTA-177, with another, different corn plant, the resulting progeny having one half of the nuclear genotype of P129-wx.

9. A seed corn blend comprising a mixture of male sterile hybrid corn seed and the synthetic hybrid corn seed of claim 1.

10. Corn grain produced by the process of:
    (a) planting, in pollinating proximity, seeds of synthetic hybrid corn plant P129-wx, Deposit No. PTA-177, and seeds of a male sterile corn hybrid;
    (b) cultivating corn plants resulting from the planting;
    (c) allowing the P129-wx corn plants to pollinate the male sterile hybrid corn plants; and
    (d) harvesting the resulting corn grain from all plants.

11. The method of claim 10 wherein the seeds of a male sterile corn hybrid have a waxy background.

12. Corn silage produced by the process of:
    (a) planting, in pollinating proximity, seeds of synthetic hybrid corn plant P129-wx, Deposit No. PTA-177, and seeds of a male sterile corn hybrid;
    (b) cultivating corn plants resulting from the planting;
    (c) allowing the P129-wx corn plants to pollinate the male sterile hybrid corn plants; and
    (d) harvesting the resulting grain parent plants for use as corn silage.

13. A synthetic corn seed designated P129A-wx, a representative sample of which has been deposited with the ATCC under Deposit No. PTA-178.

14. A synthetic corn seed designated P129B-wx, a representative sample of which has been deposited with the ATCC under Deposit No. PTA-179.

15. A corn plant produced from a seed of claim 1 having the ability to impart desirable grain quality traits to a first generation grain when used as a pollinator in the TOPCROSS® grain production system.

16. A corn plant produced from a seed of claim 1 having the ability to impart a high oil level to a first generation grain when used as a pollinator in the TOPCROSS® grain production system.

17. A corn plant derived from a seed of claim 1 and retaining the ability to impart a high oil level to a first generation grain when used as a pollinator in the TOPCROSS® grain production system.

* * * * *